United States Patent [19]
Bird et al.

[11] Patent Number: 5,817,457
[45] Date of Patent: Oct. 6, 1998

[54] METHODS AND KITS FOR DETECTING VIRAL REVERSE TRANSCRIPTASE ACTIVITY IN A SAMPLE USING AN ACIDIC PH OR AN ELEVATED TEMPERATURE

[75] Inventors: Robert E. Bird, Rockville; Audrey Chang-Yeh, Columbia, both of Md.

[73] Assignee: MA BioServices, Inc., Rockville, Md.

[21] Appl. No.: 597,774

[22] Filed: Feb. 7, 1996

[51] Int. Cl.[6] .............................. C12Q 1/70; C12Q 1/68; C12P 19/34; C07H 21/02

[52] U.S. Cl. ................................. 435/5; 435/6; 435/91.1; 435/91.2; 536/23.1; 536/24.33

[58] Field of Search ................................. 435/5, 6, 91.1, 435/91.2; 536/23.1, 24.33; 935/77, 78, 82

[56] References Cited

U.S. PATENT DOCUMENTS

| | | | |
|---|---|---|---|
| 5,187,060 | 2/1993 | Cerutti et al. | 435/5 |
| 5,310,652 | 5/1994 | Gelfand et al. | 435/6 |
| 5,407,800 | 4/1995 | Gelfand et al. | 435/6 |

OTHER PUBLICATIONS

Dorothy E. Schumm "Essentials of Biochemistry, F. A. Davis Company, Philadelphia" pp. 15–17, 1988.

Bradford, M.M. "A Rapid and Sensitive Method for the Quantitation of Microgram Quantities of Protein Utilizing the Principle of Protein–Dye Binding," *Analytical Biochemistry* (1976) 72:248–254.

Busso, M. et al., "Development of an assay that detects transcriptionally competent human immunodificiency virus type one particles," *Journal of Virological Methods* (1994) 470:129–140.

Cann, A.J. et al., "Human T–Cell Leukemia Virus Types I and II," Virology, 2nd Ed., ed. by B.N. Fields, D.M. Knipe et al. Raven Press, Ltd., New York © 1990:1501–1528.

Coffin, J.M. "Retroviridae and Their Replication," Virology, 2nd Ed., ed by B.N. Fields, D.M. Knipe et al. Raven Press, Ltd., New York © 1990:1437–1500.

Grigoryan, M.S. et al., "Activation of putative transposition intermediate formation in tumor cells," *The EMBO Journal* (1985) 4(9):2209–2215.

Heneine, W. et al., "Detection of Reverse Transcriptase by a Highly Sensitive Assay in Sera from Persons Infected with Human Immunodeficiency Virus Type 1," *The Journal of Infection Diseases* (1995) 171:1210–1216.

Hirsch, M.S. et al., "Human Immunodeficiency Virus Biology and Medical Aspects," Chapter 54, Virology, 2nd Ed., ed. by B.N. Fields, D.M. Knipe et al. Raven Press, Ltd., New York © 1990:1545–1570.

Innis, M.A. et al., PCR Protocols—A Guide to Methods and Applications, Academic Press (1990) (Table of Contents only).

Kornberg, A. et al., DNA Replication, 2nd Ed., W.H. Freeman and Company, New York (1992) p.151–152, p. 209.

Lisby, G. "Search for an HTLV–I–like retrovirus in patients with MS by enzymatic DNA amplification," *Acta Neurol. Scand.* (1993) 88:385–387.

Lugert, R. et al., "Specific Suppression of False–Positive Signals in the Product–Enhanced Reverse Transcriptase Assay," *BioTechniques* (Feb. 1996)20:210–217.

Losikoff, A.M. et al., "Industrial Experience with the Detection of Retroviruses," *Develop. biol. Standard* (19920 76:187–200.

Moore, W.A. "Experience in Cell Line Testing," *Develop. biol. Standard* (1992) 76:51–56.

(List continued on next page.)

Primary Examiner—Ardin H. Marschel
Assistant Examiner—Jezia Riley
Attorney, Agent, or Firm—Morrison & Foerster LLP

[57] ABSTRACT

Improved assay for the detection of viral reverse transcriptase activity using PCR conducts the reverse transcription reaction at an acidic pH or elevated temperature. The assay is useful in testing a wide variety of biological products and tissue samples.

22 Claims, 16 Drawing Sheets

OTHER PUBLICATIONS

Pyra, H et al., "Ulrasensitive retrovirus detection by a reverse transcriptase assay based on product enhancement," *Proc. Natl. Acad. Sci. USA* (Feb. 19940 91:1544–1548.

Reddy, E.P. et al., "Amplification and Molecular Cloning of HTLV–I Sequences from DNA of Multiple Sclerosis Patients," *Science* (Jan. 1989) 243:529–533.

Roy–Burman, P. et al., "Assay For Type C Virus in Mouse Sera Based on Paticulate Reverse Transcriptase Activity," *Journal of Virology* (Sep. 1976) 19(3):1107–1110.

Silver, J. et al., "An RT–PCR assay for the enzyme activity of reverse transcriptase capable of detecting single virions," *Nucleic Acids Research* (1993) 21(15):3593–3594.

METHODS AND KITS FOR DETECTING VIRAL REVERSE TRANSCRIPTASE ACTIVITY IN A SAMPLE USING AN ACIDIC PH OR AN ELEVATED TEMPERATURE

FIELD OF THE INVENTION

The present invention relates to the field of molecular biology and provides methods for the detection of retroviral contamination in biological samples. In a preferred embodiment, the invention provides a method to detect viral reverse transcriptase activity using the polymerase chain reaction to amplify the product of a reverse transcription reaction under conditions which allow the discrimination between true reverse transcriptase activity and apparent activity from cellular polymerases.

BACKGROUND

The safety of biological products produced in mammals, mammalian tissues, and mammalian cells depends on the availability of reliable sensitive assays for detecting contaminating materials including viral contaminants. Potential contamination of biologicals used for therapeutics poses a significant hazard for not only the patient receiving these materials, but also health care providers preparing and administering the materials. Additionally, viral contamination of biologicals used for diagnostic assays can significantly affect the results obtained with the particular assay being performed. Likewise, reliable sensitive assays which detect viruses will be useful as diagnostics as well. The most frequent viral contaminants detected in cell substrates used to produce biological products are retroviruses (Moore, 1992).

The Retroviridae comprise a large number of viruses known to infect many species, including humans. They have been associated with leukemias and lymphomas (Cann and Chen, 1990); immunodeficiencies (Hirsch and Curran, 1990); and other diseases such as Multiple Sclerosis (Reddy et al., 1989; Lisby, 1993). There are only two retroviral subfamilies that are known to be pathogenic for humans (Cann and Chen, 1990; Hirsch and Curran, 1990). These are the leukemia viruses, HTLV-1 and HTLV-2, and the immunodeficiency viruses, HIV-1 and HIV-2. However, it is clear that there are many additional retroviruses with a wide host range which can infect primates and may pose a threat to the human population. These viruses may be either primate or non-primate in origin such as the murine amphotropic and xenotropic retroviruses. Furthermore, retroviruses have a high mutation and recombination rate and can rapidly alter their host range by these mechanisms(Coffin, 1990). Therefore, it is prudent to develop tests for retroviruses that may be present in biological samples, such as, but not limited to cellular products, either natural or recombinant, human tissue biopsies and fluids.

The enzyme reverse transcriptase (RT) is found in all retroviral particles. Hence, assays that detect RT activity have been used to test for the presence of retroviruses in biological materials. Retroviral reverse transcriptase is an enzyme which can copy either RNA or DNA using either an RNA or DNA primer. Other viruses, such as Hepatitis B also have enzymes with reverse transcriptase activity. DNA polymerases, on the other hand, normally only copy DNA. However, some DNA polymerases including eukaryotic DNA polymerase γ (Kornberg and Baker, 1992a), *Thermus aquaticus* DNA polymerase (Pyra et al., 1994), and *Escherichia coli* DNA polymerase I (Kornberg and Baker, 1992b) have some ability to copy RNA. In order to avoid false positives in an RT assay that complicate the interpretation of assay results, one must be careful to distinguish true viral RT activity from that contributed by cellular DNA polymerases.

Numerous RT assays exist that measure the incorporation of radiolabeled deoxyribonucleoside triphosphates (e.g., $^3$H-TTP) into DNA using RNA as a template (Roy-Burman et al., 1976). The simplest of assays measures the incorporation of radiolabeled thymidine triphosphate into newly synthesized cDNA catalyzed by RT on a template such as poly (rA) using an oligo(dT) primer. The radiolabel incorporated is measured in a scintillation counter or by autoradiography. A threshold or background level of incorporation is established to define a positive result (Losikoff et al., 1992a). To determine whether DNA polymerase activity is present in the test article, a reaction is performed using poly(da) template and oligo(dT) primer. A high level of thymidylate incorporation into DNA in this reaction indicates the presence of DNA polymerase in the test article. When this occurs it is not possible to conclude that the RT activity seen is due to the presence of true RT because these polymerases can also utilize the poly(rA) template to some degree and mask true RT activity. Therefore, an assay with true specificity is required.

Several assays to measure RT activity using the polymerase chain reaction (PCR) to amplify product also have been developed (Pyra et al., 1994; Heneine et al., 1995; Busso and Resnick, 1994; Silver et al., 1993). The use of PCR (see Innis et al., 1990) increases the sensitivity of detection by several orders of magnitude when compared to the conventional incorporation-based assays. The first step of the RT-PCR assay is reverse transcription of an RNA template, either viral or synthetic using a complementary DNA primer and the RT activity of the sample to be tested. Test samples or controls, buffer, salts, and nucleotides are added and the sample is incubated. The temperature of this incubation is usually between 37° C. and 45° C. and the pH is usually between pH 8.0 and pH 8.5. A necessary step after the RT reaction is the removal of RNA, usually by ribonuclease treatment, to prevent the introduction of false positives due to the low level RT activity of the Taq polymerase. Subsequently, a second reverse primer is added along with Taq polymerase and the 'cDNA' product of the RT reaction is amplified by PCR. If RT activity is present in the test sample, an amplified RT-PCR product will be generated and can be detected by gel electrophoresis, ELISA or Southern blot. These assays increase the sensitivity of detection of RT activity by as much as $10^5$–$10^6$ fold. However, coincidental with this increase in sensitivity is an increase in false positive reactions coming from contaminating cellular DNA polymerases, such as polymerase γ which has been shown to have RT-like activity (Kornberg and Baker, 1992a).

Although some steps can be taken to eliminate the contaminating DNA polymerases, the release of these polymerases from lysed cells and cellular debris often make interpretation of RT assays impossible. One approach to reducing false positives involves the addition of activated DNA to RT reactions. See, Lugert et at. (1996).

What has been needed for the detection of viral reverse transcriptase is a simply assay with true specificity and that eliminates the need for additional reagents and procedures beyond those normally available to laboratories capable of performing conventional PCR assays.

SUMMARY OF THE INVENTION

It is an object of the present invention to provide an assay for the detection of viral reverse transcriptase in a sample which includes the step of adjusting the pH of the sample to an acidic range, incubating the sample with RNA templates, template-specific oligonucleotide primers and deoxyribonucleoside triphosphates sufficient to produce cDNA in the presence of reverse transcriptase activity. The cDNA so produced is amplified by the polymerase chain reaction. Subsequently, the presence and quantity of amplified cDNA relative to an appropriate control can be detected, thereby determining the presence and level of viral reverse transcriptase activity. It is a further object of the present invention to provide assays in which the pH of the sample is adjusted to a range of about 4.0 to about 6.5, more preferably about 4.5 to about 6.0, and most preferably about 5.0 to about 5.5. The assay of the present invention can be used on samples selected from a wide variety of animal and human patient samples or diagnostic and therapeutic commercial products, such as primary cell cultures, continuous cell lines, cell lysates, cell extracts, cell culture media, biological products expressed or otherwise produced in animal and mammalian cells, purified biological products, and animal and human tissues and fluids including lymph, blood, saliva and lymphocytes.

It is a further object of the invention to detect viral reverse transcriptase activity in a wide range of viruses including HTLV-1, HTLV-2, HIV-1, HIV-2 and Hepatitis B. The assay of the present invention also permits the skilled artisan to discriminate between viral reverse transcriptase activity, such as from a retrovirus, and cellular or other sources of reverse transcriptase activity present in a sample to be tested.

It is yet a further object of the invention to provide an improvement to conventional RT-PCR assays for the detection of viral reverse transcriptase activity in which the pH is adjusted to a range as described above.

Yet another object of the present invention is to provide an assay capable of discriminating between viral reverse transcriptase activity and cellular or other extraneous or contaminating reverse transcriptase activities found in a sample by adjusting the temperature or pH of the sample to a level at which the signal produced by cellular reverse transcriptase activity is substantially reduced relative to the activity of the viral reverse transcriptase activity.

Other objects of the invention will be apparent to those skilled in the art from the following discussion.

DESCRIPTION OF THE DRAWING AND FIGURES

FIG. 1. (A): Schematic diagram of an RT-PCR assay. The thin wavy line represents the MS2 phage RNA template which the RT-1 primer (short bold arrows) anneals. The RT components are listed and the newly synthesized cDNA is depicted by the horizontal bold line. The PCR components are then added and the conditions for PCR are listed. (B): Titration of purified RT with an RT-PCR assay. The 112 bp PCR product is indicated by the arrow. Primers are shown with an arrow. The No RNA represents a sample without the MS2 RNA template and serves as a negative control for reagents for the PCR. The 100 bp marker (Gibco) serves as a molecular weight marker for the gel.

FIG. 2. Cell extract and cell supernatant of infected/uninfected cell lines. Cell extracts and cell supernatants were prepared as describe below and tested for RT from the retrovirus infected γ2 DAP cells and the uninfected NIH/3T3 cells. Lane (1) cell extract, (2) cell supernatant, (3) cell supernatant with $10^{-4}$ unit RT (Superscript II), (4) cell extract without MS2 RNA, and (5) cell supernatant without MS2 RNA. (M) 123 bp ladder marker.

FIG. 3. Effect of temperature on the RT-PCR assay. AMV RT, NIH/3T3 cell extracts, and γ2 DAP cell extracts were tested in the assay with a one hour RT reaction at varying temperatures and the products electrophoresed on a 2.5% MetaPhor agarose gel. Lane (1) 37° C., (2) 45° C., (3) 50° C., (4) 55° C., (5) 37° C. without RNA. Note that the γ2 DAP cell extract no RNA negative control (5) is not shown. It was electrophoresed on another gel and was negative for the 112 bp PCR product.

FIG. 4. Effect of decreasing pH in the RT reaction mix (NIH3T3 and γ2 DAP cells) (A) Cell extracts from the uninfected NIH/ 3T3 cells and γ2 DAP cells were tested for RT at varying pH's as described. The pH at which the RT reaction was performed is listed at the top of the gel. The sample without RNA which serves as the negative control (neg) and the 100 bp marker (marker) are indicated. (B) Cell supernatants from NIH/3T3 cells and γ2 DAP cells were tested for the presence of RT at varying pH's. (M) 123 bp ladder marker.

FIG. 5. Effect of decreasing pH in the RT reaction mix (Raji and SRV infected Raji cells) Cell extracts from (A) the uninfected Raji cells and (B) SRV infected Raji cells were tested for RT at varying pH's as described. The pH at which the RT reaction was performed is listed at the top of the gel. The sample without RNA which serves as the negative control (neg) and the 123 bp marker (marker) are indicated.

(C) Effect of pH in the RT reaction mix (H9 and SIV infected H9 cells) Cell supernatant and cell extracts were prepared from H9 cells and SIV infected H9 cells as described. Lanes 1–12 are samples from H9 cells and lanes 13–20 are samples from SIV/H9 cells. H9 supernatant pH 8.3 (lane 1), with spike (lane 5), and no RNA (lane 9). H9 supernatant pH 5.5 (lane 2), with spike (lane 6), and no RNA (lane 10). H9 cell extract pH 8.3 (lane 3), with spike (lane 7), and no RNA (lane 11). H9 cell extract pH 5.5 (lane 4), with spike (lane 8), and no RNA (lane 12). SIV/H9 cell supernatant pH 8.3 (lane 13) and no RNA (lane 17), SIV/H9 cell supernatant pH 5.5 (lane 14) and no RNA (lane 18), SIV/H9 cell extract pH 8.3 (lane 15) and no RNA (lane 19), and SIV/H9 cell extract pH 5.5 (lane 16), and no RNA (lane 20). M represents the lane with the 123 bp MW marker.

FIG. 6. Titration of the RT Rauscher MLV Using the RT-PCR assay. A purified prep of Rauscher MLV viral particles was serially diluted and five microliters of each dilution was tested for RT activity at (A) pH 8.3 or (B) pH 5.5 A sample without RNA (NEG) to serve as the negative control and the 123 bp MW marker (marker) are noted.

FIG. 7. Titration of purified RT using the RT-PCR assay. M-MLV RT was serially diluted and tested (A) at pH 8.3 or pH 5.5. (B) AMV RT was serially diluted and tested at pH 5.5 in the presence of 0.5 micrograms BSA. (C) HIV RT from two commercial sources were serially diluted and tested at pH 5.5 in the presence of 0.5 micrograms of BSA. The 123 bp marker (M) and the no RNA negative control (neg) are indicated.

FIG. 8. Detecting RT from Virus in human plasma samples. Human plasma with or without 15 μl of unlysed R-MLV (average titer $4.3 \times 10^6$ pfu/ml) added was tested for the presence of RT at pH 5.5 under the conditions outlined in the text. Lanes 1–6 represent plasma samples from pellets obtained from a one hour 40K ultracentrifugation. Lane (1) plasma (2) plasma+spike (3) plasma No RNA negative control (4) plasma+virus (5) plasma+virus+spike (6) plasma+virus No RNA negative control. Lane (7) plasma tested directly (no ultracentrifugation) (8) $10^{-3}$ units of RT to serve as positive control (9) plasma+spike (10) plasma No RNA negative control. (M) 100 bp ladder marker. The spike used was 1 µl of $10^{-1}$ dilution of lysed R-MLV.

FIG. 9. Using RT-4 and RT-5 as Primers in RT-PCR assays and Restriction Enzyme Analysis. (A) AMV RT was serially diluted in buffer A and added to the reverse transcriptase mix that included 0.5 µg of BSA. The upper panel represents samples reverse transcribed at pH 8.3 and the lover panel at pH 5.5. Lane (1) $10^{-2}$ units, (2) $10^{-4}$ units, (3) $10^{-6}$ units, (4) $10^{-8}$ units, (5) $10^{-10}$ units (M) 100 bp ladder marker (b) 10 µl from the $10^{-2}$ units reaction was digested with the restriction endonuclease Eco R1. Lanes 1 and 2 are from the pH 8.3 reaction and lanes 3 and 4 are from the pH 5.5 reaction. Lanes 1 and 3 are undigested and lanes 2 and 4 are digested. The sizes of the expected molecular weights are indicated. (M) 100 bp ladder marker.

DETAILED DESCRIPTION OF THE INVENTION

Figure 1A:
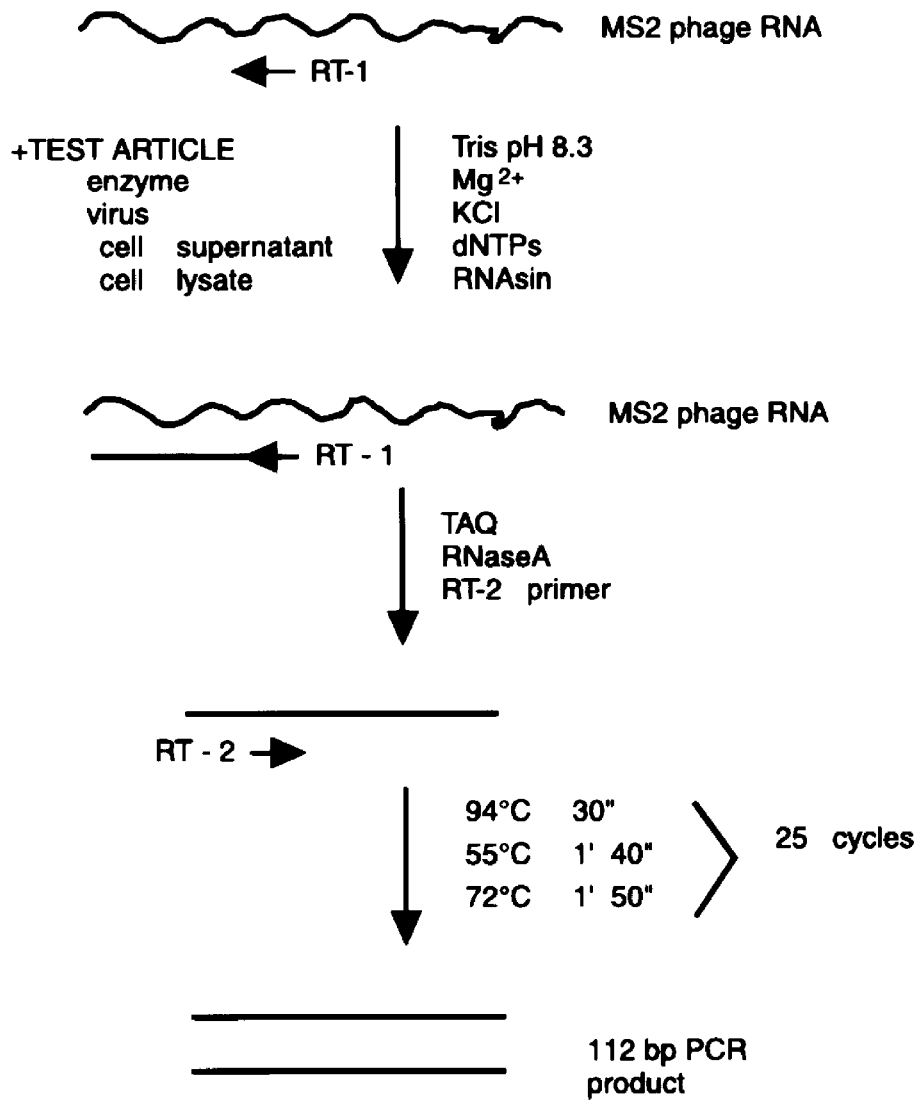

The invention described herein is a PCR based RT detection assay that easily allows discrimination between contaminating DNA polymerases and true virally encoded RT activity.

One skilled in the art can select conditions of template/ primer, buffer, salts, nucleotides, temperature and pH to perform an RT reaction, generally at pH 8.0–8.3 and at 37°–45° C. The reverse transcriptase that tests the reaction as a control can be added exongenously from any purified reverse transcriptase enzyme or from a detergent extract from a retrovirus preparation, either purified or crude, for example, simply retrovirus infected cells. Once conditions are established which demonstrate RT activity at the desired level of sensitivity, samples can then be tested to determine whether there is RT activity as a result of contamination or by infection. One skilled in the art can also apply the method of polymerase chain reaction to amplify the product of the RT reaction to increase the overall sensitivity of RT detection by amplification of the cDNA product of the RT reaction. This RT-PCR assay can then be tested for its fidelity with test articles or samples known to contain cellular polymerases which can cause false positives for RT detection.

The RT Assay: Reverse Transcription: Bacteriophage MS2 genomic RNA (Boehringer Mannheim) annealed with the primer RT-1 is used as the primer/template for the RT reaction (Pyra et al., 1994). Primer/template for a single reaction is prepared by mixing 0.28 pmoles (0.3 µg) of MS2 RNA with 10 pmoles (72 ng) RT-1 in $H_2O$, heating at 85° C. for 5 minutes and then immediately placing the tube at 37° C. for 30 minutes. The annealed RNA is then placed at 4° C. for 5 minutes. Annealed RNA is routinely made in an amount equivalent to 50 reactions (14 pmoles RNA to 500 pmoles RT-1), stored at −20° C., and used in one reaction aliquots (1.4 µl). Generally the RT-PCR reaction is performed in a mixture containing 56 mM Tris (pH 8.3), 56 mM KCl, 9.2 mM $MgCl_2$, 11.2 mM DTT, 0.1 unit/µl recombinant RNasin (Promega), 0.13 µg/ml Bovine Serum Albumin (BSA) (New England Biolabs), 1 mM of each dNTPs (Promega). Primer/template, 1.4 µl, is added to 23.6 µl RT buffer in a PCR tube. The RT source (ranging from 1 µl to 5 µl) is added last. The mixture is incubated at 37° C. for one hour.

Surprisingly, we have found that changing the pH of the RT reaction by substituting various buffers in a range of pH from about 4.0 to 6.5, preferably about 4.5 to 6, most preferably about 5.0 to 5.5, allowed the discrimination between RT activity and activity from cellular polymerases and other non-viral enzymes. In view of our discovery, as explained herein, one skilled in the art could vary the pH with other conventional buffers with pKas in the acidic range including glycine, acetate, or even phosphate to alter the pH and to optimize conditions for a particular sample or species of viral reverse transcriptase. In addition, the range of pH for each buffer used may not fall exactly within the ranges stated above but one skilled in the art can easily determine the appropriate range.

Equally surprising was the finding that increased temperature of the RT reaction also allowed discrimination between RT and cellular polymerase activity. Therefore, one skilled in the art also will now be able to find temperature conditions that discriminate between RT and cellular polymerase activity with the reaction conditions and testing conditions under consideration. In addition, it is contemplated that other reaction components such as ions and salts can and will be varied to find the exact conditions as well for discrimination between true viral RT activity and false positives caused by the presence of other polymerases, such as DNA polymerases that effect reverse transcription. Therefore, this invention is not limited to just pH or temperature modifications.

PCR amplification: To each RT reaction, 75 µl PCR mix [10 µl 10 ×PCR Buffer (Perkin Elmer), 1 µl dNTP mix (25 mM), 5 µl $MgCl_2$ (25 mM), 2 µl of RT-1 (10 pmoles/µl ), 3 µl of RT-2 primer (10 pmoles/µl), 0.1 µl Rnase A (0.1 mg/µl), 53.9 µl $H_2O$] is added along with 7.5 units Taq polymerase (Perkin-Elmer). The PCR (minus Taq) mix can be made in 10 reaction batches and stored at −20° C. The Taq polymerase should be added to the PCR mix just prior to use. For a thermocycler that does not have a heated lid (Ericomp for example), a drop of mineral oil is overlayed on the sample. The samples are then directly placed in the thermocycler and depending on which thermocycler, amplified with the conditions stated in Table 1. Clearly, one skilled in the art can choose appropriate primers for the amplification of the RT product and the template/primers chosen to be tested herein were chosen for expediency and should not be considered to be unique. In fact, we have chosen another set of primers, RT-4 and RT-5, described below, and performed the RT-PCR assay with the same sensitivity that was obtained with the previous primer set.

TABLE 1

| Modified RT-PCR Assay PCR Conditions | | | |
|---|---|---|---|
| Ericomp Thermocycler | | Perkin Elmer Model 2400 | |
| Step | Temperature (°C.) | Time (sec) | Temperature (°C.) | Time (sec) |
| Denaturation | 94 | 30 | 94 | 15 |
| Annealing | 55 | 100 | 55 | 50 |
| Extension | 72 | 110 | 72 | 55 |
| Final Extension | 72 | 600 | 72 | 240 |

In general, the assay involves the production of cDNA by RT under conditions that inactivate cellular polymerases. This cDNA is amplified by PCR to enhance its detection. This elimination of false positives caused by cellular polymerases and the enhancement of product by PCR allows the detection of very few molecules of RT. An essential feature of one embodiment of the invention which affords this discrimination is performance of the RT reaction at acidic pH. RT-PCR reactions are typically performed in a buffer with pH 8.3. Losikoff et al., (1992) have examined the effect of pH, between pH 7.7–8.3, on the reverse transcriptase and DNA polymerase activities found in extracts from cell lines infected with Rauscher murine leukemia virus, xenotropic murine leukemia virus, mink cell focus virus or squirrel monkey xenotropic retrovirus. Little if any effect on the activity of either enzyme was observed in the range tested. The effects of high temperature, >45° C., or acidic pH on the relative activities of reverse transcriptases and cellular polymerases have not been previously reported.

The reverse transcription reaction of this invention is performed at an acidic pH, preferably at about pH 4.0 to 6.5, more preferably at about pH 4.5 to 6 and most preferably at about pH 5.0 to 5.5. As a result, the activity from cellular DNA polymerases disappears with a concomitant 100 fold decrease in sensitivity for RT. However, this is still 100–10,000 fold more sensitive than the currently employed non-PCR based RT assays. This decrease in sensitivity of our assays may be made up by screening blots of the product with a radiolabeled detection technique.

Additional improvements over conventional techniques for a given sample will include changing the endpoint of the assay to a simple agarose gel, reducing the RT incubation time to one hour, prehybridization of primer/template, the addition of protease inhibitors, combining the RNase digestion with the PCR amplification of product, and lowering the pH in the RT reaction or otherwise changing the reaction conditions to discriminate between RT and cellular polymerase activity. In view of the present disclosure, the skilled artisan will be able to vary these parameters in order to optimize the results consistent with those described herein. Now under conditions described in the invention, it is possible to assay for retrovirus RT activity at a sensitivity level several logs greater than the conventional assays without generating false positives from contaminating cellular polymerases. The ease of preparing the samples in performing the assay (one template, one divalent cation, no radioactive/organic reagents, no ultracentrifugations) relative to published techniques and the wide range of retrovirus RT that can be assayed, gives the assay of the invention tremendous potential for use as a screening procedure for retroviruses in many settings including human diagnostics.

The invention can be used to detect viral RT, and hence retroviruses, in a variety of test articles including primary cell cultures, continuous cell lines, cell lysates, cell extracts, cell culture medium, biological products made in mammalian cells, purified biological products, and human tissues and fluids including lymph, blood, and saliva. The presence of RT activity in these test articles is an indication of the presence of a retrovirus and makes the clear distinction between viral RT and activity from cellular polymerases.

We have conducted a conventional RT-PCR assay for the detection of RT in test articles (or samples). This assay when performed on purified M-MLV reverse transcriptase shows a $10^5$ fold increase in sensitivity over conventional assays. The detection limit for this assay, as defined by visualization of the 112 bp PCR band by high resolution agarose gel electrophoresis, is $10^{-9}$ units of RT when the RT reaction is performed at pH 8.3. The detection limit of the radionucleotide incorporation-based RT assay is between $10^{-4}$ and $10^{-3}$ units of this enzyme. The negative controls, i.e., no RT and no MS2 RNA template, do not produce the 112 bp band, indicating that no contaminating DNA or contaminating RT activity from the Taq polymerase or RNasin was present. The sensitivity obtained with the high resolution agarose gel is comparable to the ELISA and Southern blot methodology (Pyra et al., 1994) and is preferred for its simplicity.

Figure 2:
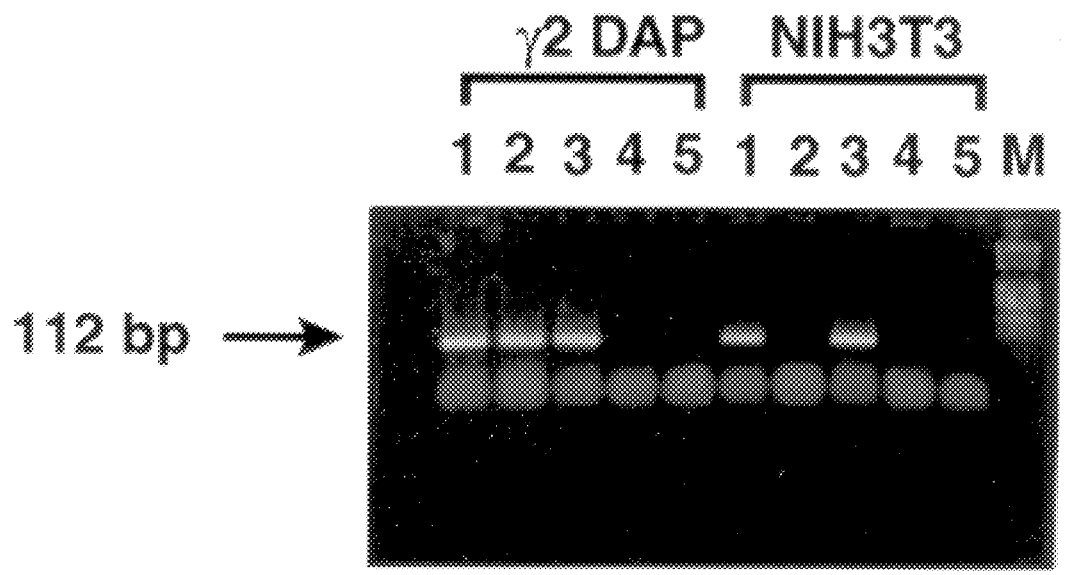

However, when the RT reaction is run at pH 8.3, the assay is susceptable to the same false positives as the other RT-PCR assays and is limited to detecting retrovirus in "clean" culture supernatants. This point is illustrated in Example 2. Performance of the RT-PCR assay at pH 8.3 generates a false positive result when NIH/3T3 extracts are assayed (FIG. 2). Since the NIH/3T3 cell line does not harbor infectious retrovirus, and expression of full length endogenous virus IAPs is low (Grigoryan et al., 1985), the RT activity seen in the NIH/3T3 cells was assumed to be a result of cellular DNA polymerases. It is clear that even though steps can be taken to minimize cellular polymerase contamination in cell preparations (e.g., low speed centrifugation, harvesting frequently fed cultures), it is not always possible to totally eliminate cellular DNA polymerases that may be released from lysed cells.

Because enzymes from different sources often have different conditions for optimal activity, we sought conditions of either pH, temperature, or both which allow the distinction between viral RT and cellular DNA polymerases. For example, if the RT reaction is performed at increasing temperatures (45° C., 50° C., and 55° C.) the activity from DNA polymerase decreases at a greater rate than that of RT. When the RT reaction is performed at 55° C., the RT activity of DNA polymerases in uninfected NIH3T3 extracts is almost completely destroyed (Example 3).

Figure 4A:
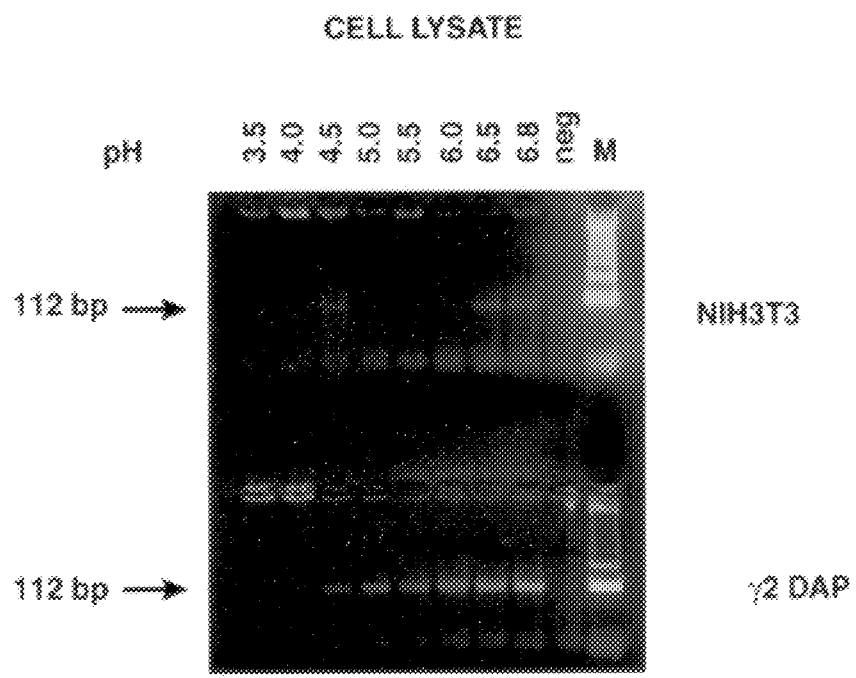

An essential feature of one embodiment of the present invention is performance of the RT reaction of our RT-PCR assay at acidic pH. In Example 3, cell extracts from the uninfected NIH/3T3 cells and retrovirally infected DAP cells were tested for RT at varying pH's from 3.5 to 6.8 as described above and the products were analyzed by electrophoresis on 2.5% Metaphor agarose gel. The results are shown in FIG. 4A. The RT activity in the NIH/3T3 extracts disappears below pH 6.5 whereas the activity in the DAP extracts where retrovirus are present does not disappear until the pH is lower than 4.5. Similar results were obtained with retrovirus infected human cell lines compared to the uninfected control (Example 5).

Along with the NIH 3T3/DAP cell line pairs, two additional uninfected/infected cell line pairs, Raji (Human B-cell transformed by Epstein-Barr Virus - ATCC No. CCL86) and Raji cells infected with Simian Retrovirus (SRV) and Human Cell Line H9 (ATCC No. HTB176) and SIV infected H9 cells, were tested for reverse transcriptase activity. The data for the latter two cell lines are presented in Example 5.

The sensitivity of the RT-PCR assay is demonstrated in Example 6. The limit of detection of RT activity for conventional incorporation assay corresponds to 1720 pfu of Rauscher MLV. Performing the RT reaction at pH 8.3, we are able to detect at a level corresponding to 0.021 pfu. Lowering the pH of the RT step to 5.5 reduces the sensitivity of the RT-PCR assay to 2.1 pfu.

The low pH RT-PCR assay eliminates false positives in a broad range of uninfected cell lines including: 293, NIH3T3, Raji, MRC-5, HeLa, CHO, BHK, LLC-MK2, H9 and Mus dunni (Example 8). Furthermore, the assay can detect an extremely wide range of retroviruses (Example 9) and can be used to detect RT in a wide range of test articles including cell culture supernatants and extracts, blood and tissues extracts. The applicability of the assay also extends to automated RT assays.

The low pH RT-PCR assay is not limited to the experimental conditions herein. For example, we contemplate that assays of different biological samples may be optimized by varying parameters of the RT and PCR steps of the assay such as temperature, buffer, divalent cation, RNA template, primer or reaction time. Example 11 demonstrates that the assay is unaffected by using different primers with the same template.

The following materials and methods were used in the experiments reflected in the examples of this specification.

Reagents: Molecular biology grade chemicals were purchased from Sigma. Stock solutions were made in diethylpyrocarbonate-treated (DEPC) $H_2O$. Protease inhibitors were purchased from Boehringer Mannheim and leupeptin and aprotinin were resuspended in DEPC treated $H_2O$ at 1 mg/ml and Pepstatin was resuspended in methanol at 1 mg/ml. Oligonucleotide primers from the MS-2 sequence (GenBank accession No. J02467) were purchased from Gibco/BRL. RT-1 (the complement of bases 108–131) [5'-d(CAT-AGG-TCA-AAC-CTC-CTA-GGA-ATG)-3'(SEQ ID NO: 1)] and RT-2 (bases 21–42) [5'TCC-TGC-TCA-ACT-TCC-TGT-CGA-G)-3'(SEQ ID NO: 1)] were used to produce a 112 base pair fragment. Alternatively, RT-5 (the complement of bases 187–210) [5'-d(TCC-AGT-CTC-ACC-GTC-CGC-GTA-AAC)-3'(SEQ ID NO:3)] and RT-4 (bases 32–51) [5'-d(TCC-CTG-TCG-AGC-TAA-TGC-CA)-3' (SEQ ID NO:4)] were used to produce a 189 base pair fragment. The RT reactions were performed with either RT-1 or RT-5 serving as primers.

Cell Cultures: All cell lines were maintained in either DMEM or EMEM supplemented with 5–10% serum, (fetal bovine or newborn calf), L-glutamine (2 mM) and, on occasion, gentamicin sulfate (0.3 µg/ml). All media and media reagents were purchased from BioWhittaker.

Sources of RT: Squirrel Monkey Retrovirus (SMRV), Equine Infectious Anemia Virus (EIAV), Rauscher Murine Leukemia Virus (R-MLV), Moloney-Murine Leukemia Virus (MMLV), Gibbon Ape Leukemia Virus (GaLV), and Adenovirus virus particles were grown in appropriate cell lines and purified from supernatants. The Rauscher Murine Leukemia Virus (R-MLV) used in these studies had an average titer of $4.3 \times 10^6$ plaque forming units per milliliter. Raji cells persistently infected with Simian Retrovirus-2 (SRV-2); H9 cells infected with Simian Immunodeficiency Virus (SIV); and LLCMK2 cells infected with Foamyvirus were made and maintained at Microbiological Associates, Inc. The Human T-cell Leukemia Virus-1 (HTLV-1) producing MT-2 cells were the source for HTLV-1 virus. A GaLV producing gibbon ape T-cell lymphoma cell line (ATCC No. HB8370) was used as a GaLV virus source. Purified RT were purchased commercially as follows: Avian Myoblastosis Virus (AMV) (Amersham), Human Immunodeficiency Virus (HIV) (Worthington), MMLV(Gibco/BRL), MuLV Superscript II (Gibco/BRL).

Sample Preparation: Cell extracts: Adherent cell lines are rinsed with ice cold PBS (Dulbecco's Phosphate Buffer Saline (D-PBS), KCl 200 mg/L, $KH_2PO_4$ 200 mg/L, NaCl 8000 mg/L, $Na_2HPO_4.7H_2O$ 2160 mg/L) and scraped in 5 mls of ice cold PBS. Cells were centrifuged at 1000×g and the resulting pellet was resuspended in 500 µl PBS (for a T75 flask - approximately $10^6$ cells) or 200 µl PBS (for a T25 flask). Suspension cells were collected by centrifugation at 1000×g and washed once with ice cold PBS, centrifuged again and the resulting pellet was resuspended in either 500 µl or 200 µl depending on the flask size. A 100 µl sample of the resuspended cell pellet was added to 100 µl of Buffer A (50 mM KCl, 25 mM Tris-HCl pH 7.5, 5 mM dithiothreitol (DTT), 0.25 mM EDTA pH 8.0, 0.025 % Triton X-100, 50% glycerol)+I (protease inhibitor cocktail containing final concentrations of aprotinin 1 µg/ml, Leupeptin 1 µg/ml, pepstatin 0.7 µg/ml). Four µl of a 2% Triton X-100 solution was added to the cell mixture (0.04% final Triton X-100 concentration). The samples were then frozen and thawed twice by changing the temperature from −70° C. to 37° C. Total protein concentration was determined using the Bio-Rad Protein assay kit (Bradford, 1976). The amount of all extracts used varied between 0.5–5 µg between experiments. When two extracts are compared the same quantity of extract was used.

Cell supernatants: Conditioned media from actively growing cells were harvested to test for RT activity in cell supernatants. The media were exposed to cells for a minimum of 72 hours before harvesting. One ml of medium was centrifuged at 3000 rpm for 5 min to clear cellular debis. One hundred µl Buffer A+I was added to 100 µl of the cleared media (cell supernatant) and 4 µl of 2% Triton X-100 was added. The sample was frozen and thawed as described above for the cell extracts.

Virus: Purified virus was diluted $10^{-1}$ in Buffer A+I with 0.04% Triton X-100 and the sample was frozen and thawed as described above. Subsequently, 10 fold dilutions were made in Buffer A+I with 0.04% Triton X- 100.

Purified RT: For all the commercially available RTs used in this study, one unit is defined as the amount of enzyme required to incorporate 1.0 nmole of deoxyribonucleotide into acid precipitable material in 10 minutes at 37° C. using a poly(rA)- oligo(dT)$_{12-18}$ template. The enzyme was diluted in Buffer A just prior to the assay.

Plasma Samples: Human blood from a single donor was collected in heparinized tubes and centrifuged at 3000 rpm for 15 minutes. The plasma was carefully collected, aliquotted, and stored at −70° C. Four hundred microliters (400 µl) of plasma alone or 400 µl plasma spiked with 15 µl unlysed R-MLV (same as described above) were filtered once through a 0.22 micron filter using a 3 ml syringe filter. The samples were placed in SW4 1 tubes (Beckman) and the tubes were filled with PBS. The samples were centrifuged at 40K for 1 hour at 4° C. The resulting pellets were resuspended in 100 µl PBS. Twenty-five microliters (25 µl) of resuspended pellet were added to 25 µl of Buffer A+I and 1 µl 2% Triton X-100 and the samples were frozen and thawed twice as described above. Twenty-five microliters (25 µl) of plasma samples were also tested directly without ultracentrifugation and lysed in the same manner.

Detection of PCR product: The PCR product is directly visualized on a horizontal 2.5% MetaPhor agarose gel (FMC BioProducts). The agarose is completely dissolved in 1× Tris-borate EDTA (TBE) (0.1M Tris borate, 0.001M EDTA) in a microwave oven, allowed to cool to 60° to 70° C., and ethidium bromide added to final concentration of 1 µg/ml. After the gel is poured, it is allowed to cool and hardened at room temperature. The gel is then placed at 4° C. for at least 30 minutes before use. Three microliters of 6× gel loading dye (Novex) is added to 10 µl of the PCR product and the mix is loaded on the gel. An appropriate DNA size marker [123 bp ladder or 100 bp ladder (Gibco/BRL)] is also utilized. The gel is electrophoresed at 100 to 150 volts for approximately one hour. The DNA bands are visualized by placing the gel on a UV transilluminator and photographed.

Restriction Enzyme Analysis: Ten microliters (10 µl) of the PCR reaction mix from the RT-4 and RT-5 primer set was digested with 10 units of Eco R1 (New England Biolabs) with the commercially supplied restriction buffer in a total reaction mix of 30 µl. Fifteen microliters (15 µl) was visualized on a 2.5% high-resolution agarose gel as described below in Example 12.

Example 1

Titration of Purified RT by RT-PCR (with an RT Performed at pH 8.3)

Figure 1B:
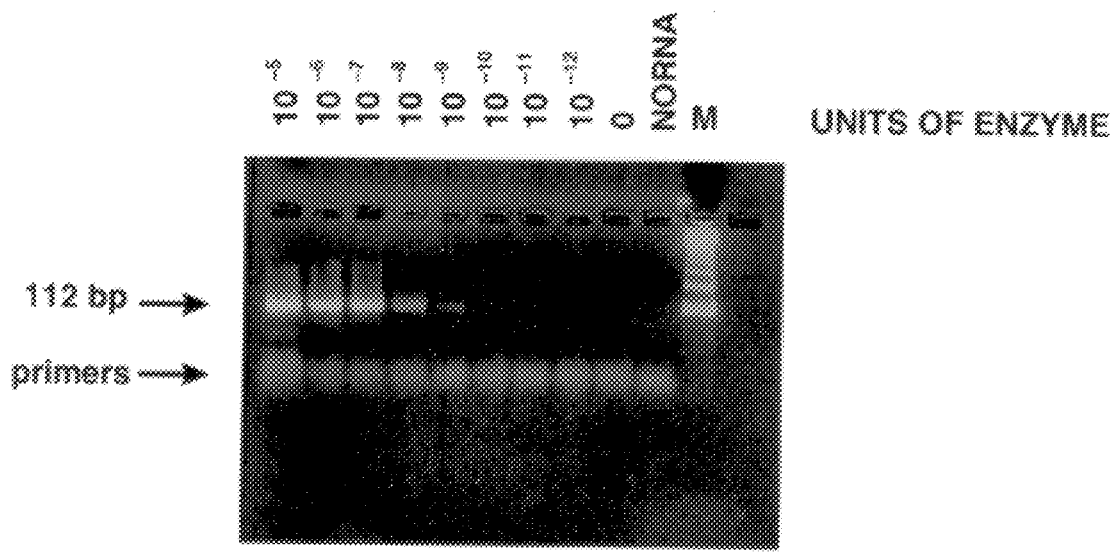

We tested the RT-PCR assay for sensitivity by diluting the recombinant M-MLV reverse transcriptase, Superscript II (Gibco-BRL) dilutions and performing the RT reaction at pH 8.3 as described above. As shown in FIG. 1B, the 112 base pair (bp) band is produced in samples which contain RT. The specific activity of the Gibco-BRL Superscript II enzyme is 350,000 units/mg of protein (Lot No. EPF40 1). The molecular weight of Superscript II is 78,000 daltons. Therefore, $10^{-9}$ units of enzyme corresponds to 22 molecules of enzymes. Other purified RT enzymes, such as Human Immunodeficiency Virus (HIV) RT, Avian Myoblastosis Virus (AMV) RT, Moloney-Murine Leukemia Virus (M-MLV) RT, all had similar limits of detection at $10^{-9}$ and $10^{-10}$ units (data not shown).

Example 2

RT-PCR Assay of Infected and Noninfected Cell Culture Supernatants and Cell Extracts The γ2 DAP (DAP) cell line (ATCC No. CRL-1949) is derived from NIH/3T3 cells and produces a recombinant retrovirus that can infect cells and reverse transcribe its genome. FIG. 2 demonstrates that both the cell supernatant (DAP Lane 2) and cell extracts (DAP Lane 1) when tested for RT activity in the presence of $Mg^{++}$ at pH 8.3, are positive. This is expected since the retrovirus particles containing RT are present in the DAP cell supernatant and the cell extract. The uninfected NIH/3T3 cell supernatant tested negative for RT in the assay (Lane NIH 2) whereas the NIH/3T3 cell extract (Lane NIH 1) tested positive. Lanes 4 and 5 are cell extract and cell supernatant without template, respectively.

Example 3

Effect of Temperature on the RT-PCR Assay

Figure 3:
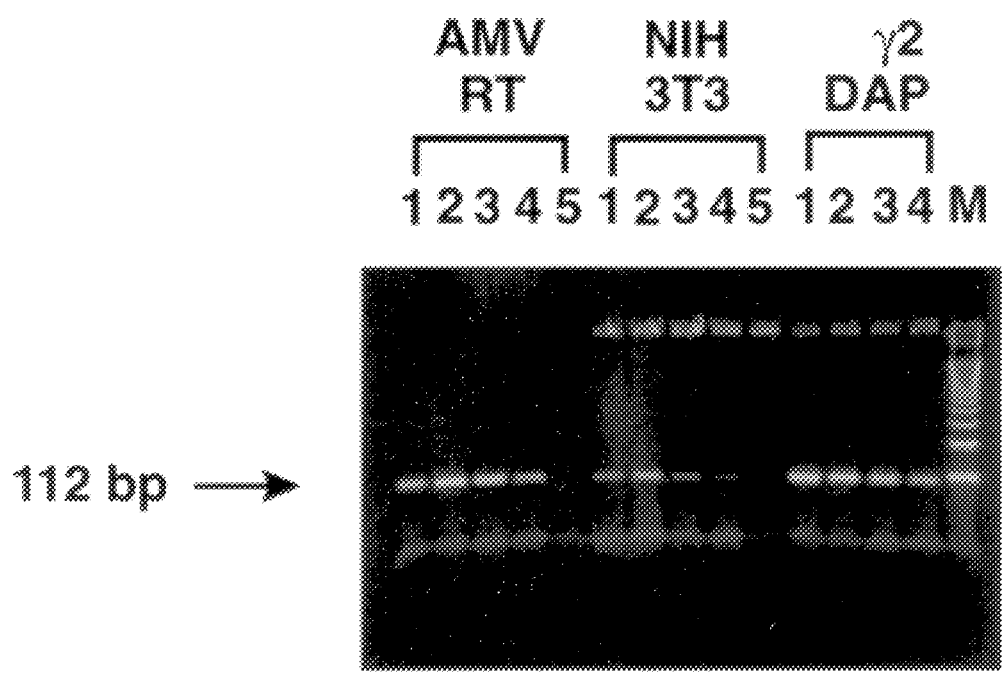

Since many RT enzymes have a higher optimal temperature than cellular polymerases, we investigated the possibility of increasing temperature of the RT reaction to exclude the contaminating activity contributed by the cellular DNA polymerases. Cell extracts from uninfected NIH/3T3 cells and the retrovirus producing μ2DAP cells were tested in the RT-PCR assay with increasing reaction temperatures. As the data in FIG. 3 illustrate, the signal produced from the uninfected cells, although not eliminated, is substantially reduced at the higher temperatures when compared with the DAP cells or the AMV RT control. By "substantially reduced" we mean that the signal produced by, e.g., uninfected cells, is decreased by greater than 75%, and preferably by greater than 90%, as compared with the signal produced by such cells at lower temperatures utilized in conventional assays. Note that at an RT reaction temperature of 55° C. (Lane 4) the activity in the NIH extract is almost completely destroyed whereas the AMV RT or DAP extract lanes show only a small diminution of the reaction at the lower temperature.

Example 4

The Effect of pH in the RT Reaction Mix (NIH/3T3 and Y2DAP Cells) on the RT-PCR Reaction Cell extracts from the uninfected NIH 3T3 cells and DAP cells were tested for RT at varying pH's from 3.5 to 6.8 as described above and the products were analyzed by electrophoresis on 2.5% Metaphor agarose gel. The results are shown in FIG. 4A. The RT activity in the NIH3T3 extracts disappears below pH 6.5 whereas the activity in the DAP extracts where retrovirus is present does not disappear until the pH is lower than 4.5.

Figure 4B:
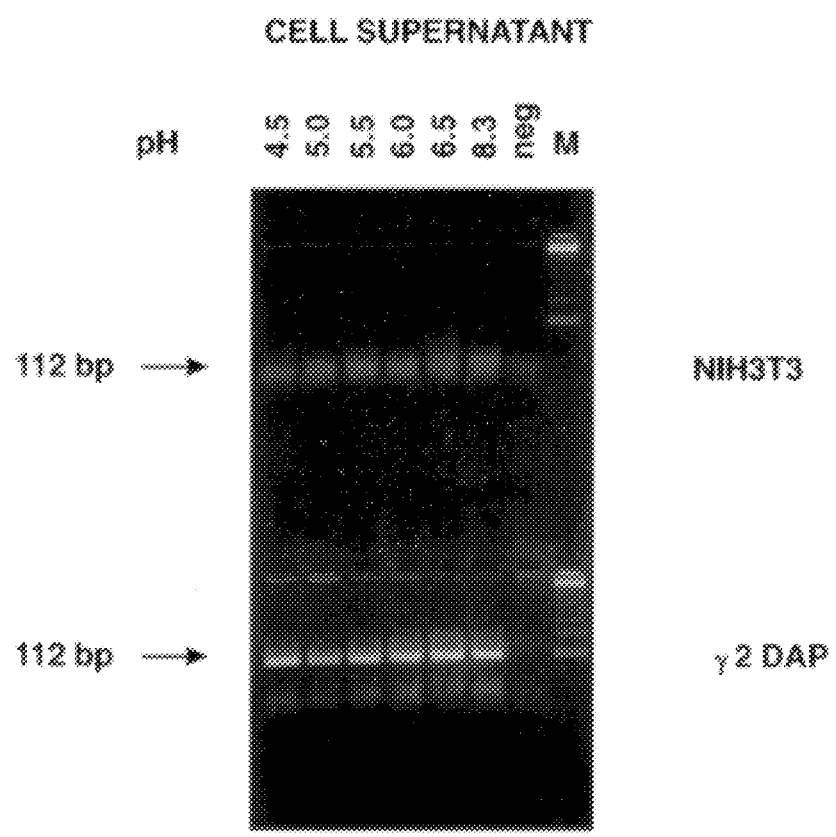

Cell supernatants from both cell lines were subjected to a pH titration analysis pH 4.5 to 8.3 (FIG. 4B). The results are shown in FIG. 4B. There is no RT activity in NIH/3T3 cell supernatants at any pH. However, there is activity in the γ2 DAP supernatant at all pHs tested resulting from the virus produced by these cells.

Example 5

Figure 5A:
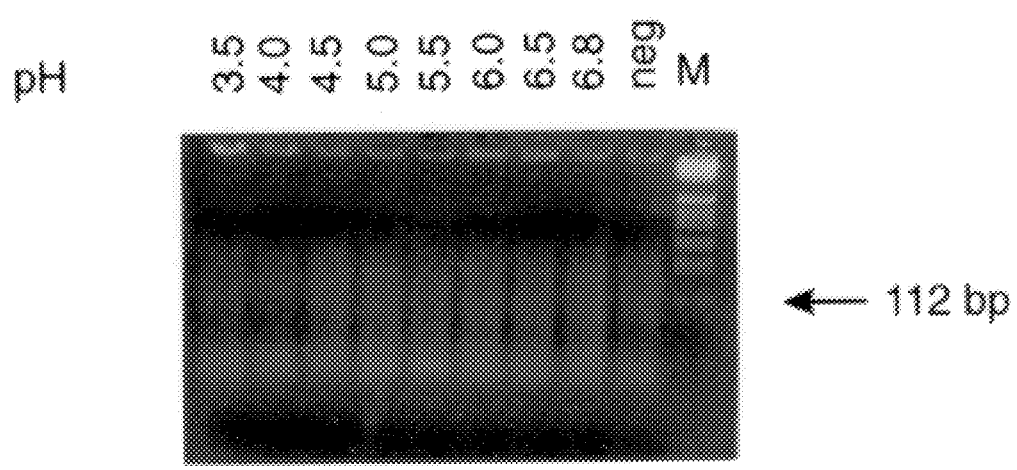

Effect of pH Titration on the RT-PCR Assay Using a Human Cell Line Infected with Non-Human Primate Retrovirus (A) (Raji cells and Raji cells infected with Simian Retrovirus (SRV-2). Cell extracts from the uninfected Raji cells and Raji cells infected with SRV-2 were tested for RT at varying pH's from 3.5 to 6.8 as described above. The products were analyzed by electrophoresis on a 2.5% Metaphor agarose gel. The results are shown in FIG. 5A. The "false positive" activity in the uninfected extracts due to cellular polymerases is not evident at pH 6.8 and below whereas the RT activity in the SRV infected cell extracts where retrovirus is stable at pH 4.5 and above.

Figure 5B:
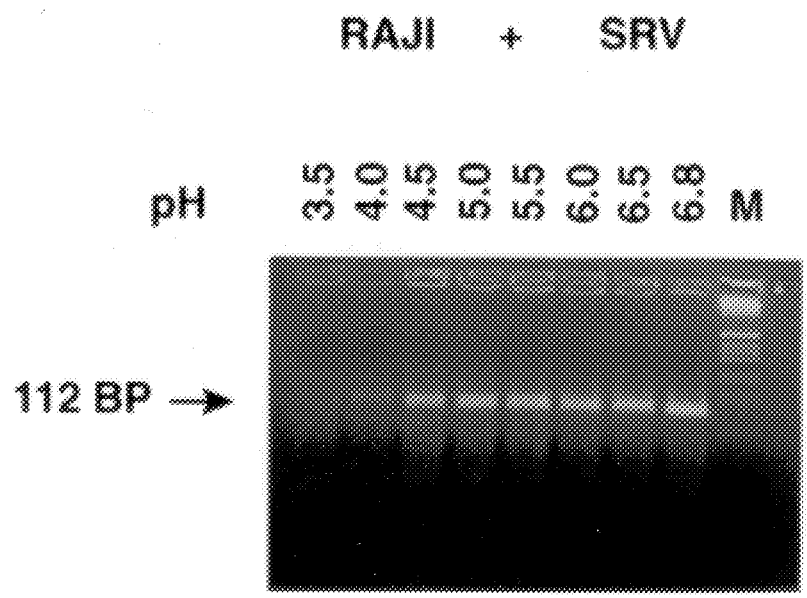

(B) H9 Cells and H9 cells infected with Simian Immunodeficiency Virus (SIV). Cell supernatant and cell extracts were prepared from H9 human T-cells and SIV infected H9 cells as described above (FIG. 5B). H9 samples were tested at pH 8.3 and pH 5.5, in the presence of spike (lysed Rauscher MLV virus particles). SIV infected H9 samples were tested at pH 8.3 and pH 5.5. A positive RT result was obtained with uninfected H9 cell extracts at the higher pH but is absent when the RT reaction is performed at pH 5.5 (Lanes 3 and 4). Both the cell lysate and supernatant from the infected cells gave positive RT results at both pH 5.5 and 8.3 (Lanes 13–16).

Example 6

Sensitivity of Detection of Rauscher MLV RT Using the RT-PCR Assay

Figure 6:
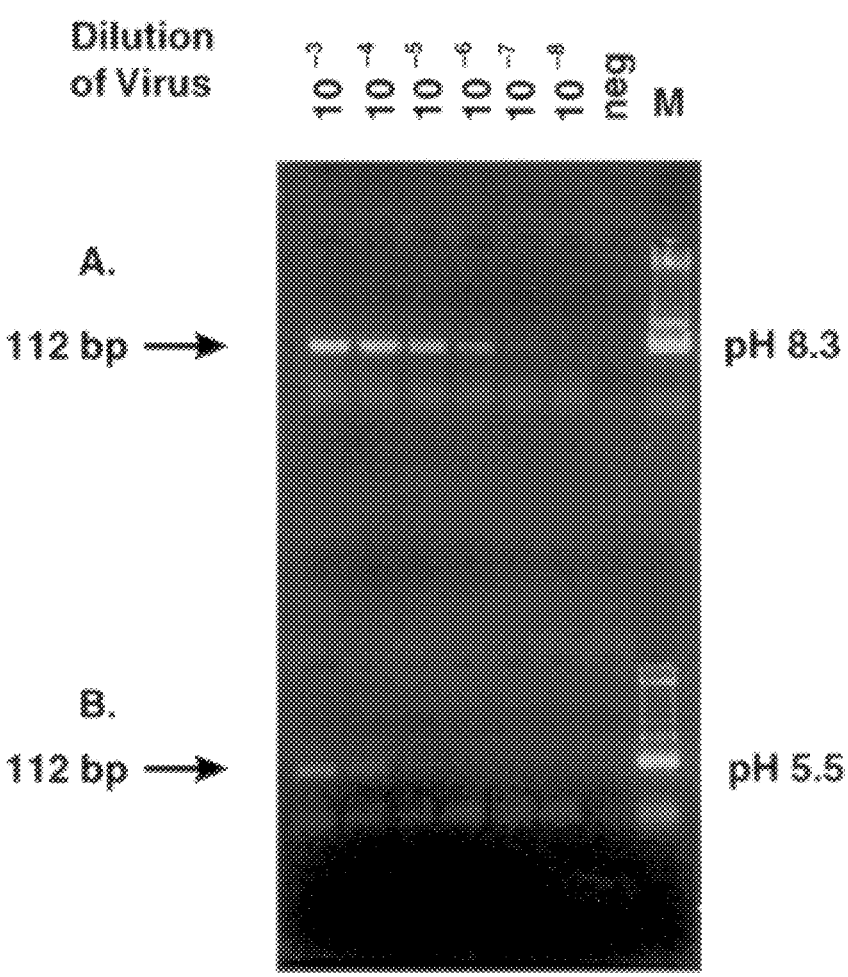

A purified preparation of R-MLV viral particles with a titer (determined by the XC plaque assay) of $4.3 \times 10^6$ pfu/ml was serially diluted and five microliters was tested for RT activity at pH 8.3 (FIG. 6A) or pH 5.5 (FIG. 6B). At 5 microliters for each dilution, $10^{-3}$ corresponds to 21.5 pfu, $10^{-4}$ to 2.1 pfu, $10^{-5}$ to 0.21 pfu, $10^{-6}$ to 0.021 pfu, and $10^{-7}$ to 0.0021 pfu.

TABLE 2

$^3$H-TTP Incorporation Assay for RT Activity
DILUTION OF R-MULV VIRAL PARTICLES

| Sample (10 μl of each dilution was tested) | cpm |
|---|---|
| R-MULV 1:2 | 18,932 |
| R-MULV 1:5 | 4,174 |
| R-MULV 1:25 | 705 |
| R-MULV 1:125 | 240 |
| R-MULV 1:250 | 123 |
| R-MULV 1:500 | 139 |
| Virus Resuspension Buffer | 155 |

The R-MLV preparation was tested in both the incorporation (Table 2) assay, and the low pH RT-PCR assay (FIG. 6B) to compare sensitivities. The numbers represent the average cpm incorporation from two separate experiments. The cutoff for a positive reaction in the $^3$H-TTP incorporation assay is 500 cpm. RT activity can be detected at dilutions up to 1:25 which corresponds to 1720 pfu. The activity in the RT-PCR (pH 5.5) can be seen at $10^{-4}$ dilution (2.1 pfu).

At the higher pH, the limit of detection was at $10^{-6}$ which corresponds to 0.021 infectious particles. At the lower pH, the limit of detection was at $10^{-4}$ dilution which corresponds to 2.1 infectious particles. The two log difference in sensitivity between the two pHs was also observed for purified RTs from AMV, HIV, and MMLV. However, it is noted that even at the lower pH the RT-PCR is still $10^3$ fold more sensitive than the radiolabel-based RT incorporation assays.

Example 7

Titration of Purified Murine, Avian and Human RT Using the RT-PCR Assay

Figure 7A:
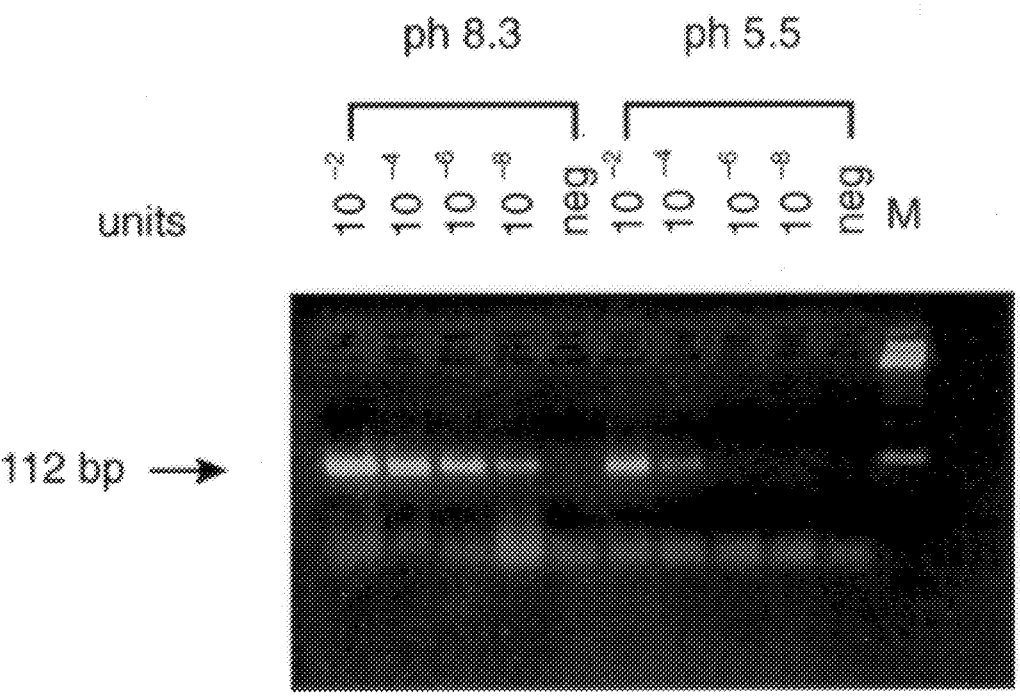
Figure 7B:
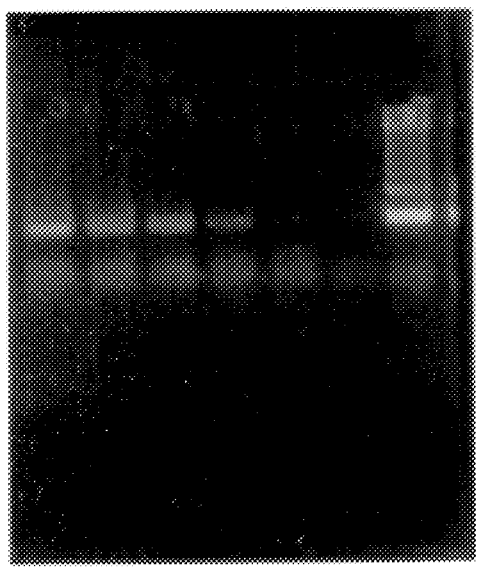
Figure 7C:
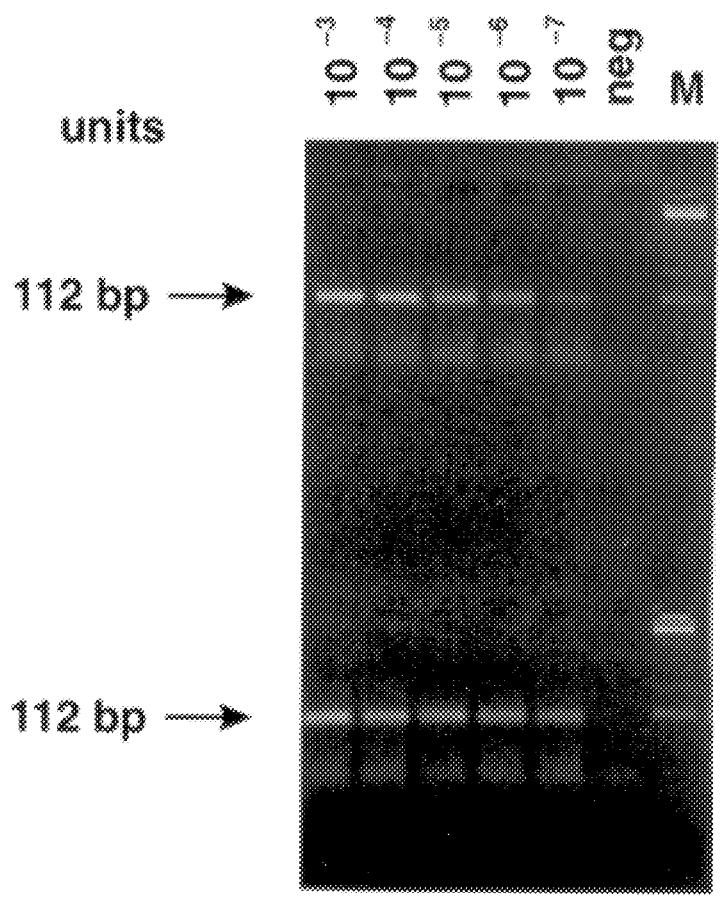

M-MLV RT was serially diluted and tested at pH 8.3 or pH 5.5 (FIG. 7A). AMV RT was serially diluted and tested at pH 5.5 in the presence of 0.5 micrograms BSA (FIG. 7B). HIV RT from two commercial sources were serially diluted and tested at pH 5.5 in the presence of 0.5 micrograms of BSA (FIG. 7C). Note that the addition of BSA to the reaction stabilizes RT activity at pH 5.5 and allows the detection of 100 fold less enzyme in this assay.

Example 8

Figure 5C:
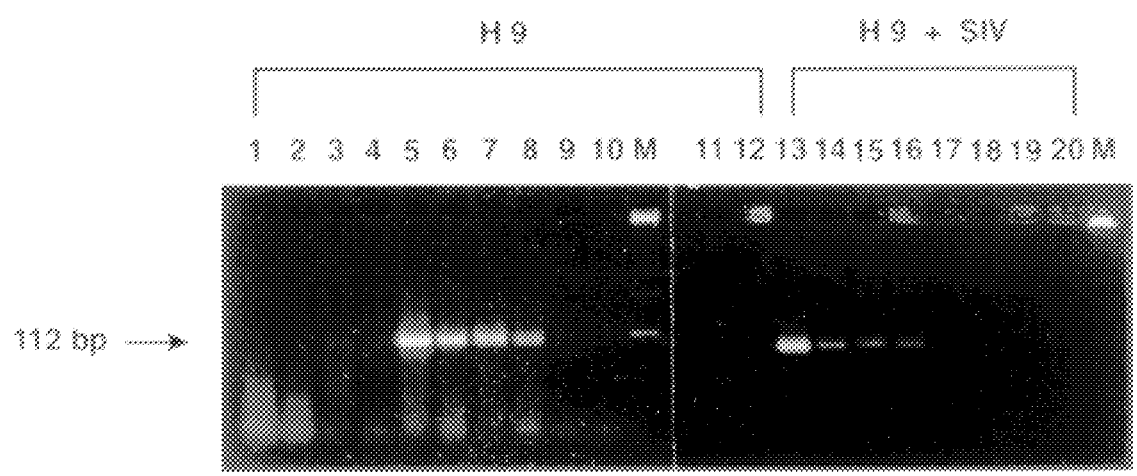

Use of the RT-PCR to Distinguish Between Cellular Polymerase and True RT Activity The results shown in FIGS. 4 and 5 demonstrate that by lowering the pH of the RT reaction buffer, only the cell extracts that harbor infectious retrovirus produce the 112 bp PCR product band whereas the uninfected cell lines do not. Table 3 summarizes the results of additional uninfected cell extracts from various sources that were prepared and tested. All were negative for RT activity at pH 5.5. The negative result is not a outcome of inhibition of RT since the presence of a RT spike results in a positive signal.

TABLE 3

Testing Uninfected Cell Lysate with RT-PCR with the RT performed at pH 8.3 or 5.5

| Cell Line | pH 8.3 | pH 5.5 | pH 5.5 + spike |
|---|---|---|---|
| 293 | + | − | n/d |
| NIH 3T3 | + | − | + |
| Raji | + | − | + |
| MRC-5 | + | − | + |
| HeLa | + | − | + |
| CHO | + | − | + |
| BHK | + | − | + |
| LLC-MK2 | +* | − | + |
| H9 | +* | − | + |
| Mus dunni | +* | − | + |

*Denotes weak signal.

Table 3. Testing uninfected cell extracts with the RT-PCR assay (RT reaction mix at pH 5.5) Cell extracts were made as described in materials and methods and tested for RT at pH 5.5. (+) indicates the presence of the 112 bp PCR product, (−) the absence of the 112 bp PCR product, and (n/d) not done. The spike was $10^{-3}$ or $10^{-4}$ units of AMV RT.

Example 9

Detection of RT Activity of Retroviruses from Multiple Species

In addition to SIV and SRV, Table 4 lists the other retroviruses RTs we have detected in our assay. Foamyvirus, Human T Cell Leukemia Virus type I, squirrel monkey retrovirus, equine infectious anemia virus, avian myeloblastosis, human immunodeficiency virus, Gibbon Ape leukemia virus, represents the different retrovirus subfamilies (Oncovirus, Lentivirus, and the Spumavirus). Purified adenovirus viral particles which do not have RT, are negative for RT by the assay. The procedure described here demonstrates that one set of conditions can detect an extremely wide range of retroviruses.

TABLE 4

Detecting Viral RT by low pH RT-PCR

| Virus or RT Species | Source | Results |
|---|---|---|
| Foamyvirus | infected cells | + |
| HTLV-I | infected cells | + |
| GaLV | infected cells | + |
| SIV | infected cell supe | + |
| SRV-2 | infected cell supe | + |
| SMRV | purified virus | + |
| EIAV | purified virus | + |
| R-MLV | purified virus | + |
| MMLV | purified virus | + |
| AMV | purified RT | + |
| HIV-1 | purified RT | + |
| MMLV | purified RT | + |
| Adenovirus | purified virus (non-retrovirus) | − |

Table 4. Testing various retrovirus for RT activity with low pH RT-PCR The source of the retrovirus are indicated and the presence of the 112 bp PCR product indicative of the RT is shown with (+) or (−).

Example 10

The Detection of RT in Viral Particles in Human Plasma

Figure 8:
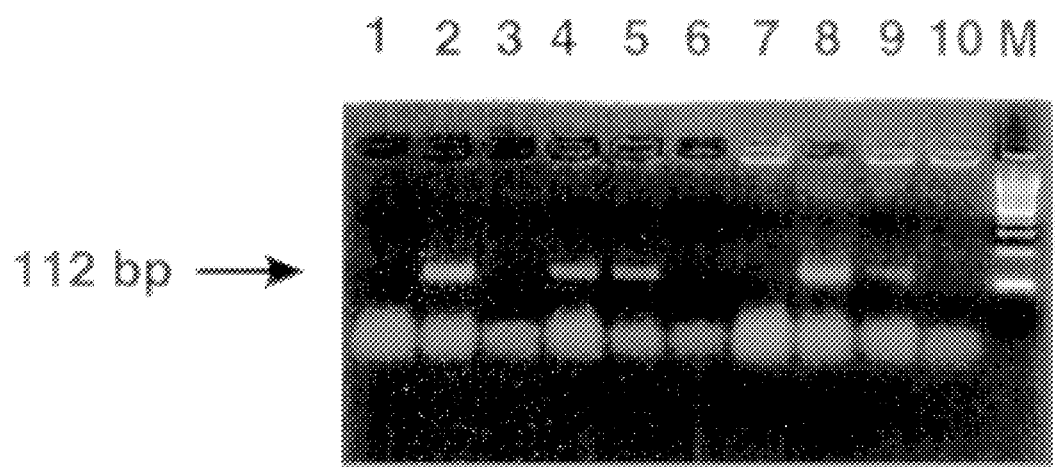

We wanted to test if we could detect RT from viral particles in human plasma. Plasma from the blood of a single healthy donor was obtained and tested. Plasma alone, and plasma with added virus particles were centrifuged at 40K for 1 hour. The resulting pellets were resuspended, lysed, and tested for the presence of RT in the manner described (FIG. 8, Lanes 1–6) with the pH 5.5 RT incubation. The results indicated that only the plasma sample with the added retrovirus gives a positive result (Lane 4) whereas the plasma sample without retrovirus is negative (Lane 1). The negative result is not due to inhibition since the presence of a spike of virus gives a positive signal (Lane 2) and the samples without the template RNA are negative (Lanes 3 and 6) which controls for PCR contamination in reagents. A plasma sample that was not centrifuged was also tested. Plasma was taken directly, lysed, and tested for RT in the same fashion. Plasma alone again gave a negative result (Lane 7) whereas in the presence of spike, the 112 bp PCR product is produced (Lanes 8 and 9). We noted that in the non-pelleted plasma sample taken directly, a gelatinous white protein precipitate forms upon PCR. This may slightly inhibit the PCR and account for the weaker signal.

Example 11

Performance of the RT-PCR with Different Primers

We investigated the performance of the assay at two pH's using different primers. The reverse transcriptase primer RT-5 lies 55 bases downstream of RT-2 from MS2 phage nucleotide 187-nucleotide 210. The PCR forward primer RT-4 lies from MS2 phage nucleotide 32-nucleotide 51.

Figure 9A:
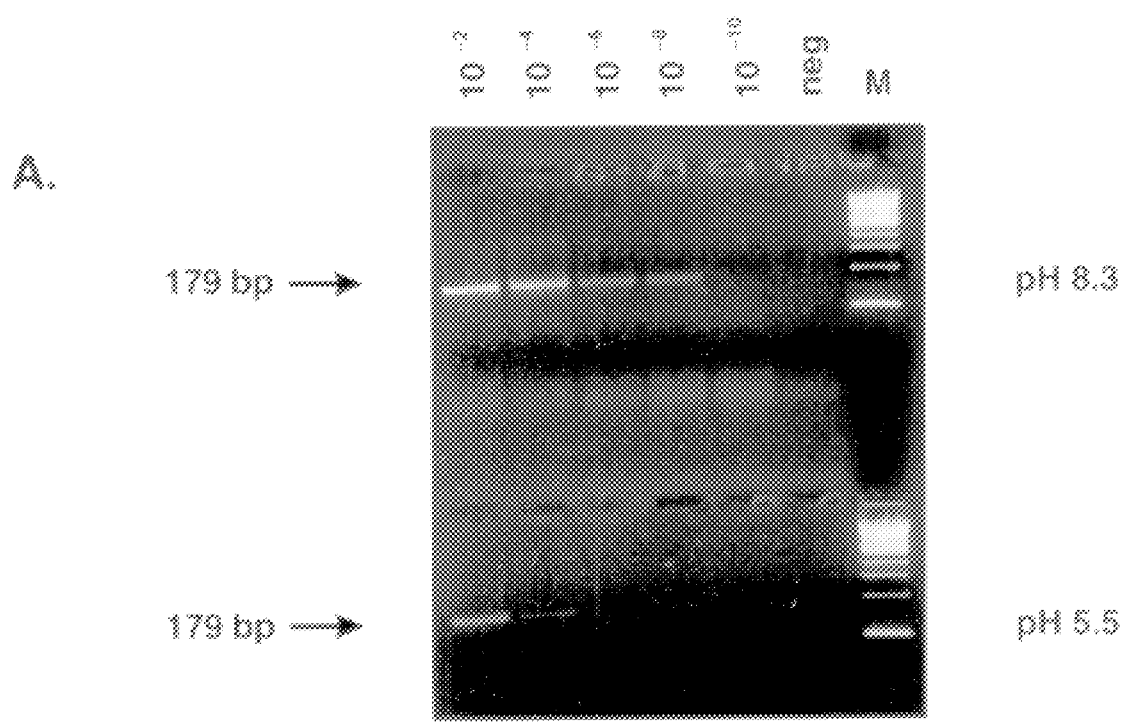
Figure 9B:
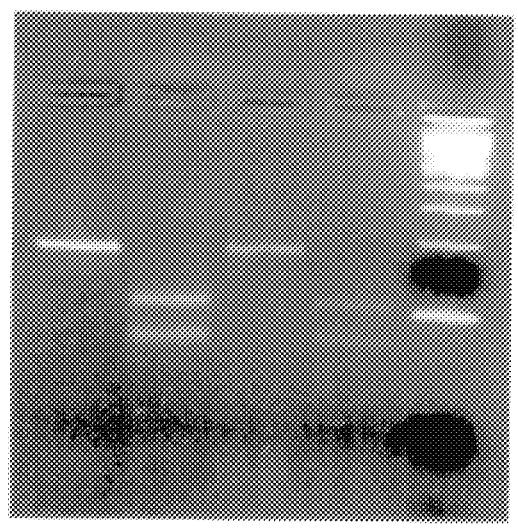

Together, RT4 and RT5 primers will generate a 179 bp PCR product from the cDNA. As FIG. 9A illustrates, the AMV RT diluted to $10^{-8}$ units at pH 8.3 and $10^{-4}$ units at pH 5.5. These sensitivities are in the same range as the results obtained with the smaller PCR product generated with RT-1 and RT-2. To confirm that the PCR product is indeed generated from MS2 sequences, the DNA was digested with the restriction enzyme Eco R1. FIG. 9B illustrates the digest of the 179 bp PCR product with Eco R1. The presence of a single Eco R1 site in the MS2 phage sequence at nucleotide 103 will digest the 179 bp product into two bands with the sizes of 72 bp and 107 bp. This diagnostic digest along with the predicted 179 bp amplicon confirms that the PCR product is generated from MS2 RNA sequences.

Example 12

Use of the RT-PCR Assay in Screening Lymphnode Biopsies

The RT-PCR described herein can also be used to screen lymphnode biopsies or other tissue biopsies for the presence of RT. Tissue is homogenized with a dounce homogenizer or other tissue homogenizer to disrupt the connective tissue and yield individual cells. The cells prepared in this manner are extracted as described and assayed for RT activity at an acidic (or low) pH. A positive result indicates the presence of a retrovirus. This detection of virus in tissue samples will be useful in the diagnosis of viral infections and will subsequently lead to treatment decisions based on whether the infection is retroviral or not.

The current assay overcomes difficulties in utilizing either conventional or the RT-PCR assays where the RT reaction is performed at high pH, around pH 8 because of the insensitivity of the former and the lack of discrimination of the latter.

Example 13

Use of the low pH RT-PCR Assay in Screening Blood

Retrovirus infections are known to occur in circulating lymphocytes, for example, infections caused by the immunodeficiency viruses. The current assay already has been shown to work in plasma and can be adapted to assay extracts of circulating lymphocytes for the presence of RT. Lymphocytes are collected by centrifugation and washed with buffer if necessary. Extracts are prepared as described above and assayed in the acidic or low pH RT-PCR assay of the present invention. A positive result indicates the presence of retrovirus. This detection of virus in tissue samples will be useful in the diagnosis of viral infections and will subsequently lead to treatment decisions based on whether the infection is retroviral or not.

The current assay overcomes difficulties in utilizing either conventional or the RT-PCR assays where the RT reaction is performed at high pH, around pH 8 because of the insensitivity of the former and the lack of discrimination of the latter.

Based on the foregoing discussion and examples, one skilled in the art readily could adapt the RT-PCR assay conditions to optimize detection of RT activity derived from a wide variety of viruses as well as a broad range of clinical samples and diagnostic or therapeutic products that potentially might contain viral RT activity. The general assay conditions for RT and for the PCR amplification of detected signal, including salinity, appropriate primers, etc., routinely can be varied in order to optimize assay results. Accordingly, the present invention is intended to be defined by the claims which follow rather than by the foregoing disclosure and examples.

We also contemplate, as part of the present invention, a test kit for performing the reverse transcriptase assay or reverse transcriptase assay together with the PCR amplification and detection aspects of the present invention. This kit would appropriately include a buffer sufficient to set a pH for the sample in the acidic ranges discussed above. Such a test kit would also include, as appropriate, RNA templates, template-specific oligonucleotide primers, deoxyribonucleoside triphosphates, salts, divalent cations, etc., sufficient to produce cDNA in the presence of reverse transcriptase activity. Moreover, the present invention also as contemplated is applicable to the testing of cells, products and tissues derived from mammals and various animals, including but not limited to primates such as human beings.

REFERENCES

The disclosures of all references mentioned in this application are hereby incorporated by reference in their entirety. These include:

U.S. Pat. No. 5,187,060 to Cerutti, et al., Detection of Influenza A Virus by PCR.

U.S. Pat. No. 5,310,652 to Gelfand, et al., Reverse Transcriptase with Thermostable DNA Polymerase-high Temperature Reverse Transcriptase.

U.S. Pat. No. 5,407,800 to Gelfand, et al., Reverse Transcriptase with Thermus Thermophilus Polymerase.

Bradford MM. (1976) A rapid and sensitive method for the quantitation of microgram quantities of protein utilizing the principle of protein-dye binding. *Anal. Biochem.* 72:248–254

Busso M., and Resnick L. (1994) Development of an assay that detects transcriptionally competent human immunodeficiency virus type one particles. *J. of Virol. Meth.* 470:129–140.

Cann A. J., and Chen I. S. Y. (1990) Human T-Cell Leukemia Virus Types I and II. *Fields Virology* eds. Fields B. N., and Knipe D. H. Raven Press Ltd., New York. pp. 1501–1528.

Coffin J. M., (1990) Retroviridae and their replication. *Fields Virology* eds. Fields B. N., and Knipe D. H. Raven Press Ltd., New York. pp. 1437–1500.

Grigoryan M. S., Kramerov A., Tulchinske E., Reasva S., And Lukanidin E. M. (1985) Activation of putative transposition intermediate formation in tumor cells. EMBO 4: 2209–2215.

Heneine W., Yamamoto S., Switzer W. M., Spria T. J., and Folks T. M. (1995) Detection of RT by a highly sensitive assay in sera from persons infected with HIV-1. *J Infect. Dis.* 171:1210–1216.

Hirsch M. S., and Curran J. (1990) Human Immunodeficiency Viruses. *Fields Virology* eds. Fields B. N., and Knipe D. H. Raven Press Ltd., New York. pp. 1545–1570.

Michael A. Innis et al., PCR Protocols - A Guide to Methods and Applications, Academic Presss (1990).

Kornberg A., and Baker T. (1992a) *DNA Replication.* W. H. Freeman and Company. San Francisco, Calif. p. 209.

Kornberg A., and Baker T. (1992b) *DNA Replication.* W. H. Freeman and Company. San Francisco, Calif.. pp. 151–152.

Lisby, G. (1993) Search for an HTLV-I-like retrovirus in patients with MS by enzymatic amplification. *Acta Neurol. Scand.* 88:385–387.

Lugert, R., König, H., Kurth, R., and Tönjes, R. R. (1996) Specific Suppression of False Positive Signals in the Product-Enhanced Reverse Transcriptase Assay. *BioTechniques* 20:210–217.

Losikoff A. M., Poiley J. A., Raineri R., Nelson R. E., and Hillesund T. (1992) Industrial experience with the detection of retrovirus. *Develop. BioL Standard* 76:187–200.

Moore, W. A. (1992) Experience in Cell Line Testing. *Develop. Biol. Standard*, 76, pp. 51–56.

Pyra H., Boni J., and Schupbach J. (1994) Ultrasensitive retrovirus detection by reverse transcriptase assay based on product enhancement. *Proc. Natl. Acad. Sci. U.S.A.* 91;1544–1548.

Reddy E. P., Sandbearg-Wollheim M., Mettus R. V., Ray P. E., DeFreitas E., and Koprowsil H. (1989) Amplification and molecular cloning of HTLV-I sequences from DNA of multiple sclerosis patients. *Science* 243:529–533.

Roy Burman P., Dougherty M., Pal B. K., Charman H. P., Klement V., and Gardner M. B. (1976) Assay for type C virus in mouse sera based on particulate reverse transcriptase activity. *J. Virol* 19:1107–1110.

Silver J., Maudru J., Fujita K., and Repaske R. (1993) A RT-PCR assay for the enzyme activity of reverse transcriptase capable of detecting single virions. *Nucl. Acids Research* 21:3593–3594.

We claim:

1. An assay for detection of viral reverse transcriptase activity in a sample, comprising the steps of:

adjusting the pH of the sample to an acidic level;

incubating the sample under said acidic pH condition, with RNA templates, template specific oligonucleotide primers and deoxyribonucleoside triphosphates sufficient to produce cDNA in the presence of reverse transcriptase activity;

amplifying the cDNA so produced by the polymerase chain reaction; and detecting the presence and quantity of amplified cDNA, thereby determining the presence and level of viral reverse transcriptase activity.

2. The assay of claim 1, wherein said pH is adjusted to a range of about 4.0 to about 6.5.

3. The assay of claim 2, wherein said pH is adjusted to a range of about 4.5 to about 6.0.

4. The assay of claim 3, wherein said pH is adjusted to a range of about 5.0 to about 5.5.

5. The assay of claim 1, wherein the sample is selected from the group consisting of primary cell cultures, continuous cell lines, cell lysates, cell extracts, cell culture media, biological products made in mammalian cells, purified biological products, and human and animal tissues and fluids including lymph, blood, saliva and lymphocytes.

6. The assay of claim 1, wherein the viral reverse transcriptase activity to be detected in the sample is selected from the group consisting of HTLV-1, HTLV-2, HIV-1, HIV-2 and Hepatitis B.

7. An assay to discriminate between viral reverse transcriptase activity and cellular reverse transcriptase activity in a sample, comprising the steps of:

adjusting the pH of the sample to an acidic level;

incubating the sample, under said acidic pH condition, with RNA templates, template specific oligonucleotide primers and deoxyribonucleoside triphosphates sufficient to produce cDNA in the presence of reverse transcriptase activity;

amplifying the cDNA so produced by the polymerase chain reaction; and detecting the presence and quantity of amplified cDNA, thereby determining the presence and level of viral reverse transcriptase activity relative to cellular reverse transcriptase activity.

8. The assay of claim 7, wherein said pH is adjusted to a range of about 4.0 to about 6.5.

9. The assay of claim 8, wherein said pH is adjusted to a range of about 4.5 to about 6.0.

10. The assay of claim 9, wherein said pH is adjusted to a range of about 5.0 to about 5.5.

11. The assay of claim 7, wherein the sample is selected from the group consisting of primary cell cultures, continuous cell lines, cell lysates, cell extracts, cell culture media, biological products made in mammalian cells, purified biological products, and human and animal tissues and fluids including lymph, blood, saliva and lymphocytes.

12. The assay of claim 7, wherein the viral reverse transcriptase activity to be detected in the sample is selected from the group consisting of HTLV-1, HTLV-2, HIV-1, HIV-2 and Hepatitis B.

13. In an improvement to an RT-PCR assay for the detection of viral reverse transcriptase activity in which a first step comprises the reverse transcription of RNA into DNA and a second step comprises the amplification of transcribed DNA by polymerase chain reaction, the improvement comprising the step of conducting the first step at an acidic pH.

14. The improved assay of claim 13, wherein said first step is conducted at a pH within the range of about 4.0 to about 6.5.

15. The improved assay of claim 14, wherein said first step is conducted at a pH within the range of about 4.5 to about 6.0.

16. The improved assay of claim 15, wherein said first step is conducted at a pH within the range of about 5.0 to about 5.5.

17. The assay of claim 13, wherein the sample is selected from the group consisting of primary cell cultures, continuous cell lines, cell lysates, cell extracts, cell culture media, biological products made in mammalian cells, purified biological products, and human and animal tissues and fluids including lymph, blood, saliva and lymphocytes.

18. The assay of claim 13, wherein the viral reverse transcriptase activity in the sample is selected from the group consisting of HTLV-1, HTLV-2, HIV-1, HIV-2, and Hepatitis B.

19. An assay to discriminate between viral reverse transcriptase activity and cellular reverse transcriptase activity in a sample, comprising the steps of:

adjusting the temperature or pH of the sample to a level at which the signal of activity produced by cellular reverse transcriptase activity in a reverse transcriptase assay is substantially reduced relative to its signal at a lower temperature or at a higher pH;

incubating the sample, under said acidic pH condition, with RNA templates, template specific oligonucleotide primers and deoxyribonucleoside triphosphates sufficient to produce cDNA in the presence of reverse transcriptase activity;

detecting the presence and quantity of cDNA so produced, thereby determining the presence and level of viral reverse transcriptase activity relative to cellular reverse transcriptase activity.

20. The assay of claim 19, wherein said detecting includes a polymerase chain reaction step.

21. The assay of claim 1 in which the pH of the sample is adjusted to a level at which the signal of activity produced by cellular reverse transcriptase activity is substantially reduced relative to its signal at a lower or conventional assay temperature or at a higher or conventional pH.

22. The assay of claim 7 in which the pH of the sample is adjusted to a level at which the signal of activity produced by cellular reverse transcriptase activity is substantially reduced relative to its signal at a lower or conventional assay temperature or at a higher or conventional pH.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CATAGGTCAA ACCTCCTAGG AATG    24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCCTGCTCAA CTTCCTGTCG AG    22

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCCAGTCTCA CCGTCCGCGT AAAC    24

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCCCTGTCGA GCTAATGCCA    20